(12) United States Patent
Israel

(10) Patent No.: US 6,524,340 B2
(45) Date of Patent: Feb. 25, 2003

(54) ACCOMMODATING INTRAOCULAR LENS ASSEMBLY

(76) Inventor: Henry M. Israel, 39 Ben Zakai Street, Bnei Brak 51482 (IL)

( * ) Notice: Subject to any disclaimer, the term of this patent is extended or adjusted under 35 U.S.C. 154(b) by 0 days.

(21) Appl. No.: 09/862,426

(22) Filed: May 23, 2001

(65) Prior Publication Data

US 2002/0177896 A1 Nov. 28, 2002

(51) Int. Cl.⁷ .................................................. A61F 2/16
(52) U.S. Cl. ...................................... 623/6.44; 623/6.41
(58) Field of Search ............................... 623/6.38, 6.39, 623/6.4, 6.43, 6.44, 6.45, 6.46, 6.47

(56) References Cited

U.S. PATENT DOCUMENTS

| | | | |
|---|---|---|---|
| 4,485,498 A | * 12/1984 | Gimbel | ..................... 623/6.39 |
| 5,476,514 A | 12/1995 | Cumming | |
| 6,013,101 A | * 1/2000 | Israel | ......................... 623/6.43 |
| 6,179,870 B1 | * 1/2001 | Sourdille et al. | .......... 623/6.39 |
| 6,302,911 B1 | * 10/2001 | Hanna | ....................... 623/6.39 |
| 6,342,073 B1 | 1/2002 | Cumming et al. | |

FOREIGN PATENT DOCUMENTS

| | | |
|---|---|---|
| FR | 2784575 A | 4/2000 |
| JP | 63279813 A | 5/1990 |
| WO | 01 64136 A | 9/2001 |
| WO | 01 66042 A | 9/2001 |

* cited by examiner

Primary Examiner—Corrine McDermott
Assistant Examiner—Hieu Phan
(74) Attorney, Agent, or Firm—David Klein; Dekel Patent Ltd.

(57) ABSTRACT

An intraocular lens assembly including a lens, a haptic, and a leverage arm connecting the lens to the haptic, wherein the leverage arm is adapted to apply a lever force on the lens acting generally along a chord inwards of a perimeter of the lens.

15 Claims, 1 Drawing Sheet

ACCOMMODATING INTRAOCULAR LENS ASSEMBLY

FIELD OF THE INVENTION

The present invention relates generally to intraocular lens (IOL) assemblies and particularly to accommodating IOL assemblies.

BACKGROUND OF THE INVENTION

Natural accommodation in a normal human eye having a normal human crystalline lens involves automatic contraction or constriction and relaxation of the ciliary muscle of the eye (and zonules controlled by the ciliary muscle) by the brain in response to looking at objects at different distances. Ciliary muscle relaxation, which is the normal state of the muscle, shapes the human crystalline lens for distant vision. Ciliary muscle contraction shapes the human crystalline lens for near vision. The brain-induced change from distant vision to near vision is referred to as accommodation.

Accommodating intraocular lens (IOL) assemblies have been developed that comprise an IOL that moves in response to ciliary muscular contraction and relaxation, thereby to simulate the movement of the natural lens in the eye, and, inter alia, help provide patients with better focusing ability.

One example of an accommodating IOL assembly is described in U.S. Pat. No. 5,476,514 to Cumming, the disclosure of which is incorporated herein by reference. Cumming describes an accommodating IOL with plate haptics for implantation within the capsular bag of the eye, after removal of the natural lens by an anterior capsulotomy. During a postoperative healing period following surgery, anterior capsular remnants fuse to the posterior capsule of the bag by fibrosis about the plate haptics, and the lens is deflected rearward to a distant vision position against the elastic posterior capsule of the bag in which the posterior capsule is stretched rearward. After fibrosis is complete, natural brain-induced contraction and relaxation of the ciliary muscle relaxes and stretches the fused remnants and increases and reduces vitreous pressure in the eye to effect vision accommodation by the fused remnants, the posterior capsule, and vitreous pressure.

Haptics are clearly defined in the art as the interface elements of the IOL that touch the eye structure ("haptic" is from the Greek word for touch). It is noted that in Cumming, movement, contraction or tensioning of the haptics causes the lens movement. This is a drawback because the mechanical behavior of the haptics is affected by the boundary conditions between the haptics and the eye structure. These boundary conditions are not well defined and may not be constant, since they arise from the amount and nature of the fibrosis about the plate haptics.

Another example of an accommodating IOL assembly is described in U.S. Pat. No. 6,013,101 to Israel, the disclosure of which is incorporated herein by reference. The IOL assembly includes at least two, preferably rigid, linkage arms, i.e., haptics, each being attached to the optic at a first position on the arm thereof and cooperating with ciliary muscle or the zonules at a second position on the arm. There are at least two pivots, one of which is rotatably attached to each respective haptic intermediate the first and second positions.

U.S. Pat. No. 6,013,101 discusses the difference between what it calls "rigid" haptics or linkage arms and "flexible" or "resilient" haptics. Resilient haptics comprise resilient wires formed of plastics or any other biologically inert material, which are sufficiently stiff so that when a compressive force is applied thereto, they distort but do not buckle or collapse. When compressed, resilient haptics cause the artificial lens to translate anteriorly along the optical axis (anterior-posterior axis). When the compressive force is reduced, the resilient haptics spring back under their own elasticity so as to return the lens to its original position.

Rigid haptics, on the other hand, do not deform significantly under the compressive or tensile forces present during accommodation. They are, therefore, capable of transmitting forces applied to them more efficiently than flexible elements and potentially with greater mechanical advantage. It is in this context that the term "rigid" is to be understood throughout the disclosure. It should be understood, however, that "rigid" haptics may be made of very thin material and may not be rigid under other circumstances, such as during surgical implantation, when greater force is applied to them so that they can be inserted into the lens capsule.

However, the mechanical behavior of the haptics of U.S. Pat. No. 6,013,101 is also affected by the boundary conditions between the haptics and the eye structure.

SUMMARY OF THE INVENTION

The present invention seeks to provide an improved accommodating IOL assembly. In contrast to the prior art, in the present invention, the haptic does not apply leverage to the artificial lens. Rather one or more leverage arms, which connect the haptic to the lens, apply the requisite lever force to the lens to impart accommodating motion to the lens. In one embodiment of the invention, the leverage arm applies a lever force along a chord inwards of the perimeter of the lens. In other words, the leverage arm has a significantly greater "reach" and mechanical advantage than prior art accommodating IOLs, which rely on circumferentially attached haptics to apply leverage to the lens.

Thus, in the present invention, accommodating movement of the lens is accomplished by applying the lever force from the leverage arm, which force is generally independent of the boundary condition of the haptic. The haptic of the present invention is preferably a ring haptic.

There is thus provided in accordance with a preferred embodiment of the present invention an intraocular lens assembly including a lens, a haptic, and a leverage arm connecting the lens to the haptic, wherein the leverage arm is adapted to apply a lever force on the lens acting generally along a chord inwards of a perimeter of the lens.

In accordance with a preferred embodiment of the present invention the leverage arm has a longitudinal axis, and a first end attached to the haptic and a second end attached to the perimeter of the lens offset from the longitudinal axis.

Further in accordance with a preferred embodiment of the present invention the first end of the leverage arm is generally symmetric about the longitudinal axis.

Still further in accordance with a preferred embodiment of the present invention the second end of the leverage arm includes two attachment zones generally symmetric about the longitudinal axis. The chord may connect the two attachment zones and intersect the longitudinal axis between the first end and a center of the lens.

In accordance with a preferred embodiment of the present invention the two attachment zones have a span of at least 90° therebetween with respect to a center of the lens.

Further in accordance with a preferred embodiment of the present invention the leverage arm is configured generally as a plate. The haptic may be shaped generally like a ring.

There is also provided in accordance with a preferred embodiment of the present invention a method for causing movement of a lens of an intraocular lens assembly, the method including attaching a lens to a haptic with a leverage arm, and causing movement of the lens by applying a lever force from the leverage arm on the lens generally independent of a boundary condition of the haptic. The movement of the lens is preferably generally along an anterior-posterior ocular axis.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
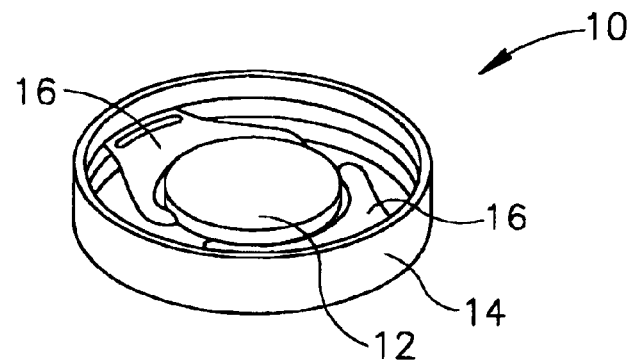
FIGS. 1, 2 and 3 are simplified pictorial, planar view and sectional illustrations, respectively, of an intraocular lens (IOL) assembly, constructed and operative in accordance with a preferred embodiment of the present invention, FIG. 3 being taken along lines III—III in FIG. 2.
Figure 2:
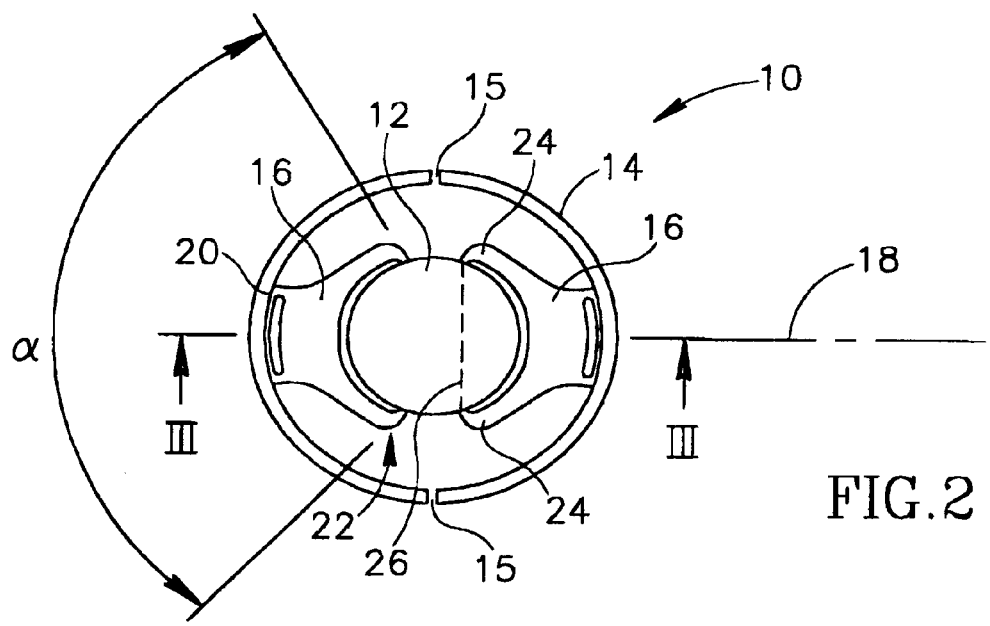
Figure 3:
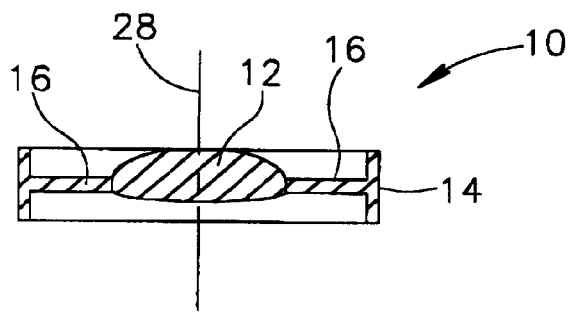

Reference is now made to FIGS. 1–3, which illustrate an intraocular lens (IOL) assembly 10 constructed and operative in accordance with a preferred embodiment of the present invention.

IOL assembly 10 preferably includes a lens 12 and one or more haptics 14. In the illustrated embodiment, there is one haptic 14 shaped generally like a ring, which may optionally have one or more splits 15 (this option being shown in FIG. 2 only). It is understood that this is just one example of a suitably shaped haptic and other sizes and shapes of haptics may be used as well. One or more leverage arms 16 connect lens 12 to haptic 14. In the illustrated embodiment, there is a pair of leverage arms 16 symmetric about lens 12. As seen in FIG. 3, whereas leverage arms 16 may be attached at the center of the thickness of haptic 14, lens 12 may be attached to leverage arms 16 offset anteriorly or posteriorly from the center of the thickness of haptic 14.

IOL assembly 10 is preferably constructed of a clear, transparent, biologically compatible material, such as but not limited to, polymethylmethacrylate (PMMA), silicone, silicone rubber, collagen, hydrogel, hyaluronic acid (including the sodium, potassium and other salts thereof), polysulfones, thermolabile materials and other relatively hard or relatively soft and flexible biologically inert optical materials.

Each leverage arm 16 is preferably configured generally as a plate and has a longitudinal axis 18. A first end 20 of leverage arm 16 is preferably attached to haptic 14 and a second end 22 may be attached to the perimeter of lens 12 offset from longitudinal axis 18. The first end 20 of leverage arm 16 may be generally symmetric about longitudinal axis 18. The second end 22 of leverage arm 16 may include two attachment zones 24, which are generally symmetric about longitudinal axis 18.

Each leverage arm 16 is adapted to apply a lever force on lens 12 acting generally along a chord 26 inward of the perimeter of lens 12. Specifically, each leverage arm 16 acts as a torque or moment transfer device that transfers ciliary muscle relaxation or contraction into a force on lens 16, which causes lens 12 to generally translate either anteriorly for near vision (generally as a result of ciliary muscle contraction) or posteriorly for distant vision (ciliary muscle relaxation), generally along an anterior-posterior ocular axis 28 (FIG. 3).

As seen in FIG. 2, chord 26 preferably connects the two attachment zones 24, and intersects longitudinal axis 18 between the first end 20 and the center of lens 12. In other words, leverage arm 16 is preferably not attached to the equator of lens 12 (i.e., the intersection of axis 18 with haptic 14), but rather at zones 24 on the circumference of lens 12 between the poles (i.e., the points 90° from the equator) and the equator of lens 12. Each leverage arm 16 has a significantly greater "reach" and mechanical advantage than prior art accommodating IOLs, which rely on circumferentially attached haptics to apply leverage to the lens. The force transferred by leverage arms 16 is generally independent of the boundary condition of haptic 14.

In accordance with one embodiment of the present invention, the two attachment zones 24 have a span of an angle a therebetween with respect to the center of lens 12. In the illustrated embodiment, the angle a is at least 90°, and may be at least 130°.

It will be appreciated by person skilled in the art that the present invention is not limited by what has been particularly shown and described herein above. Rather the scope of the present invention is defined only by the claims that follow:

What is claimed is:

1. An intraocular lens assembly comprising:

a lens;

a haptic; and a leverage arm connecting a perimeter of said lens to said haptic, wherein said leverage arm is adapted to apply a lever force on said lens acting generally along a chord inwards of a perimeter of said lens.

2. The intraocular lens assembly according to claim 1 wherein said leverage arm has a longitudinal axis, and a first end attached to said haptic and a second end attached to the perimeter of said lens offset from said longitudinal axis.

3. The intraocular lens assembly according to claim 2 wherein said first end of said leverage arm is generally symmetric about said longitudinal axis.

4. The intraocular lens assembly according to claim 2 wherein said second end of said leverage arm comprises two attachment zones generally symmetric about said longitudinal axis.

5. The intraocular lens assembly according to claim 4 wherein said chord connects said two attachment zones.

6. The intraocular lens assembly according to claim 1 wherein said leverage arm has a longitudinal axis and wherein said chord intersects said longitudinal axis.

7. The intraocular lens assembly according to claim 2 wherein said chord intersects said longitudinal axis between said first end and a center of said lens.

8. The intraocular lens assembly according to claim 4 wherein said two attachment zones have a span of at least 90° therebetween with respect to a center of said lens.

9. The intraocular lens assembly according to claim 1 wherein said leverage arm is configured generally as a plate.

10. The intraocular lens assembly according to claim 1 wherein said haptic is shaped generally like a ring.

11. The intraocular lens assembly according to claim 10 wherein said haptic has at least one split formed therein.

12. The intraocular lens assembly according to claim 1 and comprising a plurality of said leverage arms.

13. A method for causing movement of a lens of an intraocular lens assembly, the method comprising:

attaching a perimeter of a lens to a haptic with a leverage arm; and causing movement of said lens by applying a lever force from said leverage arm on said lens generally independent of a boundary condition of said haptic.

14. The method according to claim 13 wherein said causing movement comprises causing movement of said lens generally along an anterior-posterior ocular axis.

15. The method according to claim 13 wherein said applying said lever force comprises applying said lever force generally along a chord inwards of a perimeter of said lens.

\* \* \* \* \*